United States Patent
Weber-Unger et al.

(10) Patent No.: US 6,623,523 B2
(45) Date of Patent: *Sep. 23, 2003

(54) SYMMETRICAL BREAST PROSTHESIS

(75) Inventors: Georg Weber-Unger, Kufstein (AT); Stephan Volk, Miesbach (DE)

(73) Assignee: F + E Gesellschaft fur, Bekleidungsinnovation GmbH & Co. KG, Brannenburg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/340,653

(22) Filed: Jan. 13, 2003

(65) Prior Publication Data

US 2003/0105523 A1 Jun. 5, 2003

Related U.S. Application Data

(63) Continuation of application No. 09/982,945, filed on Oct. 22, 2001.
(60) Provisional application No. 60/251,048, filed on Dec. 5, 2000.

(51) Int. Cl.[7] .................................................. A61F 2/12
(52) U.S. Cl. ............................................................ 623/7
(58) Field of Search .......................................... 623/7, 8

(56) References Cited

U.S. PATENT DOCUMENTS

| 5,066,302 A | 11/1991 | Rice ................................. 623/7 |
| 5,071,433 A | 12/1991 | Naestoft et al. ................. 623/7 |
| 5,092,881 A | 3/1992 | Weber-Unger et al. ......... 623/8 |
| 5,480,429 A | 1/1996 | Weber-Unger et al ......... 623/7 |
| 6,136,028 A | 10/2000 | Weber-Unger et al. ........ 623/7 |

FOREIGN PATENT DOCUMENTS

| DE | 6 926 549 | 7/1969 |
| DE | 0 384 951 A1 | 9/1990 |
| DE | 92 01 918.8 | 6/1992 |
| DE | 44 13 076 A1 | 10/1995 |
| DE | 197 54 144 A1 | 11/1998 |
| DE | 108 38 428 A1 | 3/2000 |

OTHER PUBLICATIONS

Sales Catalog, Anita International, Post Mastectomy, 1997.
ADEV Gesellschaft fur Entwicklung und Vertrieb von medizintechnischen Artikein mbh catalog (in German); 8 pages.
Brust Prothetik catalog (in German); 1 page.
Otto Bock Medical catalog (in German); 1 page.
Otto Bock Medical catalog (in German); 6 pages.
Otto Bock Medical catalog (in German); 4 pages.
Comfort Contura catalog page (picture only); 1 page.
German Office Action in co–pending German appln No. 10059–013.6; dated Jun. 20, 2001.

*Primary Examiner*—David J. Isabella
(74) *Attorney, Agent, or Firm*—Pennie & Edmonds LLP

(57) ABSTRACT

A symmetrical, heart-shaped breast prosthesis has two identical notches which are arranged symmetrically with respect to a plane of symmetry dividing the prosthesis body into two equal halves and at an angle in the range between 30° and 90° between them, in such a way that, when the prosthesis is worn, only one of the two notches is essentially perpendicular to the longitudinal axis of the wearer's body. The notches have the effect that the prosthesis collapses slightly when the wearer is in the upright position and becomes flatter when the wearer is in the prostrate position. In the state when worn, the heart-shaped prosthesis which is symmetrical in the unshaped state becomes an asymmetrical prosthesis having a lateral branch and an upper branch which moves downwards when the wearer is in the upright position and slips upwards when the wearer is prostrate.

26 Claims, 3 Drawing Sheets

SYMMETRICAL BREAST PROSTHESIS

RELATED APPLICATIONS

This is a Continuation of application Ser. No. 09/982,945, filed Oct. 22, 2001, now U.S. Pat. No. 6,565,604, which claims priority to U.S. Provisional Application No. 60/251,048, filed Dec. 5, 2000.

FIELD OF THE INVENTION

The invention relates to a symmetrical breast prosthesis for wearing in the left or right cup of a brassiere or corselet following a mastectomy in a person.

BACKGROUND OF THE INVENTION

Breast prosthesis are known in the prior art. A prior art breast prosthesis includes a prosthesis body which has a front having the shape of a natural breast, a concave back provided with at least one elongated notch and a prosthesis edge which forms a closed line and at which the front and the back each end, the prosthesis body comprising a flexible silicone rubber material which is enclosed without cavities in a bag of elastically extensible plastics films connected tightly to one another along the prosthesis edge.

Such a breast prosthesis is disclosed in U.S. Pat. No. 6,136,028. It has a symmetrical triangular shape and can consequently be worn alternatively as a replacement for the right or left amputated breast, the notch or notches at the back of the prosthesis body running in each case transversely to the longitudinal axis of the wearer's body. Although this breast prosthesis virtually completely compensates the removed breast tissue up to the region of the armpit, it is not always felt to be optimum by prosthesis wearers because the lateral branch towards the sternum may be too long and is troublesome particularly when the prosthesis is worn in an underwired brassiere.

Another symmetrical breast prosthesis which can be worn alternatively on the left or right side of the breast has a drop-shaped outline. Such a breast prosthesis is described, for example, in German Utility Model 69 26 549. It is particularly suitable for those women in whom it has been possible to retain the upper breast attachment and it is necessary to compensate for tissue removed surgically in the armpit region. It is sometimes also worn in such a way that its branch points towards the shoulder if tissue has been removed at the upper breast attachment. Owing to its drop shape, however, it cannot simultaneously compensate surgically removed tissue in the armpit region and at the upper breast attachment.

However, symmetrical breast prostheses which have both a lateral branch and an upper branch are also known, the two branches being of equal length. These breast prostheses are approximately heart-shaped and are worn in such a way that their plane of symmetry lying between the two branches makes an angle of about 45° with the longitudinal axis of the wearer's body, one of the branches always pointing to the shoulder and the respective other branch to the armpit when the breast prosthesis is worn on the left side as well as on the right side. However, the heart-shaped breast prostheses known to date also do not always correspond to the natural conditions towards the sternum. Moreover, the branches are often too short in the direction of the armpit or too long in the direction of the shoulder.

The ideal shape of the breast prosthesis has been possessed to date only by the asymmetrical breast prosthesis which has two branches, of which the upper branch is smaller than the lateral branch. Inevitably, asymmetrical breast prostheses are formed in such a way that they can be worn either only on the left side of the body or only on the right side of the body. Since the shapes for "left" asymmetrical breast prostheses are different from the shapes for "right" asymmetrical breast prostheses, asymmetrical breast prostheses are in principle more expensive to produce than symmetrical breast prostheses, in which the side on which they are worn is in fact independent of the shapes used in production. Since asymmetrical breast prostheses can be worn either only on the left or only on the right, their stock-keeping in the trade is also more complicated than that of symmetrical breast prostheses. In comparison with symmetrical breast prostheses, it would in fact be necessary to stock twice the quantity of asymmetrical breast prostheses if affected women are to be supplied equally with symmetrical or asymmetrical breast prostheses. If breast prostheses are offered, as usual, in 10 to 15 different sizes, the double stock-keeping and hence twice the volume of asymmetrical breast prostheses compared with symmetrical breast prostheses is problematic especially in small businesses which often have very limited storage facilities. Owing to their more complicated stock-keeping, asymmetrical breast prostheses are therefore less popular than symmetrical breast prostheses in the trade.

SUMMARY OF THE INVENTION

In one aspect, the present invention is directed to a breast prosthesis of the generic type that can provide compensation for removed breast tissue at the upper and armpit-near breast attachment which is at least as favorable in terms of shape and weight as an asymmetrical breast prosthesis, but whose capability of being worn alternatively on the left or right side of the breast is unrestricted.

This achieved if the closed line formed by the prosthesis edge is heart-shaped and two identical notches are provided which are arranged symmetrically with respect to a symmetry plane dividing the prosthesis body into two equal halves and at an angle between them in the range between 30° and 90° so that, when the prosthesis is worn, only one of the two notches is essentially perpendicular to the longitudinal axis of the wearer's body.

The term "heart-shaped" should be interpreted widely. In principle, it is intended to describe the shape of a symmetrical prosthesis which has two branches which are arranged a distance apart and one of which points towards the shoulder and the other towards the armpit when the prosthesis is worn, the section of the prosthesis edge between the two branches having a more or less concave shape. Even a straight or virtually straight shape of this section of the prosthesis edge is not intended to mean that the total shape of the prosthesis in outline can no longer be designated as "heart-shaped". What is essential for the heart-shaped prosthesis is that it can be worn on the left or right side of the breast, it being merely necessary to rotate the prosthesis through 90° when the breast side is changed.

An advantage of the breast prosthesis according to the present invention is that it combines the advantages of an asymmetrical breast prosthesis with regard to comfort when worn and compensation capability with those of a symmetrical breast prosthesis with regard to changeability of side.

As in the case of the prosthesis described in U.S. Pat. No. 6,136,028 mentioned at the outset, the breast prosthesis according to the present invention collapses slightly when the wearer is in the upright position, owing to the notch effect of the notches running transversely to the longitudinal axis of the wearer's body, the upper branch slipping slightly downwards and that part of the prosthesis which corresponds to the lower region of the breast acquiring greater convexity corresponding to the natural conditions. As in the case of the breast prosthesis disclosed in U.S. Pat. No. 6,136,028, the breast prosthesis according to the present invention has the advantage that it becomes slightly flattened when the wearer is prostrate and consequently also corresponds to the natural conditions when the wearer is prostrate. Moreover, compared with other known breast prostheses without notches, the breast prosthesis according to present the invention has the advantage of improved swinging behavior and a lower weight.

Compared with the conventional asymmetrical breast prosthesis, the breast prosthesis according to the present invention has the further advantage that the symmetrical branches can be made slightly longer than in the case of the conventional asymmetrical breast prosthesis because, when the wearer is in the upright position, the upper branch slips slightly downwards owing to the collapse of the prosthesis, whereas the lateral branch remains unchanged in length and continues to extend to the armpit region, so that it can better compensate tissue removed there than the lateral branch of an asymmetrical breast prosthesis. The shortening of the upper branch of the breast prosthesis according to the present invention when the wearer is in the upright position has the effect that it does not project out of the brassiere, which is considered to be pleasant by the wearer for visual reasons.

Preferably, the two notches each extend in length along a line which passes in each case through one of the two rounded corners of the heart-shaped prosthesis contour. This has the advantage that the transition between each notch and the prosthesis edge in the longitudinal direction of the notch can be made particularly gentle because the prosthesis edge at this point is the greatest distance away from the respective notch.

Preferably, the two notches make an angle in the range of 40° to 60° with one another.

In the case of smaller prosthesis sizes, it may be advantageous if the two notches each extend in length along a line which in each case intersects the heart-shaped prosthesis contour at a point which is located laterally next to one of two rounded corners of the heart-shaped prosthesis contour. Here, it may furthermore be advantageous if the two notches make an angle of about 90° with one another. Furthermore, it may be advantageous here if the inner ends of the two notches meet the plane of symmetry.

In the case of larger prosthesis sizes, it may be advantageous if at least one further notch is provided between the two notches since each further notch improves the flattening capacity when the wearer of the prosthesis is prostrate. Each of the two notches may also be curved in the longitudinal direction.

Finally, it may be advantageous if, in addition to the two notches, further notches are provided at the back of the prosthesis body, the further notches being arranged symmetrically with respect to the plane of symmetry of the prosthesis body.

The object according to the present invention is thus also achieved if the closed line formed by the prosthesis edge is heart-shaped and is provided with a V-shaped notch which is symmetrical with respect to a plane of symmetry dividing the prosthesis body into two equal halves and has an opening angle in the range between 30° and 90° between its two limbs, only one of the two limbs of the notch being essentially perpendicular to the longitudinal axis of the wearer's body in the state when worn.

In the case of larger prosthesis sizes, it may be advantageous if, in addition to the V-shaped notch, at least one further notch is provided. The further notch, too, may be V-shaped. The V-shaped notch and/or each further V-shaped notch can in each case have a curved or rounded section between the two limbs. Furthermore, the two limbs of the V-shaped notch and/or the two limbs of each further V-shaped notch may be curved in the longitudinal direction.

The breast prosthesis according to the present invention can be noticeably reduced in weight if the silicone rubber material is mixed with a filler comprising hollow spheres which have a weight of 5 to 30% by weight, based on the weight of the silicone rubber material.

Preferably, the mixture consisting of the silicone rubber material and filler has a viscosity of 2500 to 8000 m·Pas. The hollow spheres may comprise a plastic or glass.

BRIEF DESCRIPTION OF THE DRAWINGS

The present invention is describer with reference to the attached figures in which.

DETAILED DESCRIPTION OF THE PREFERRED EMBODIMENT

Figure 1:
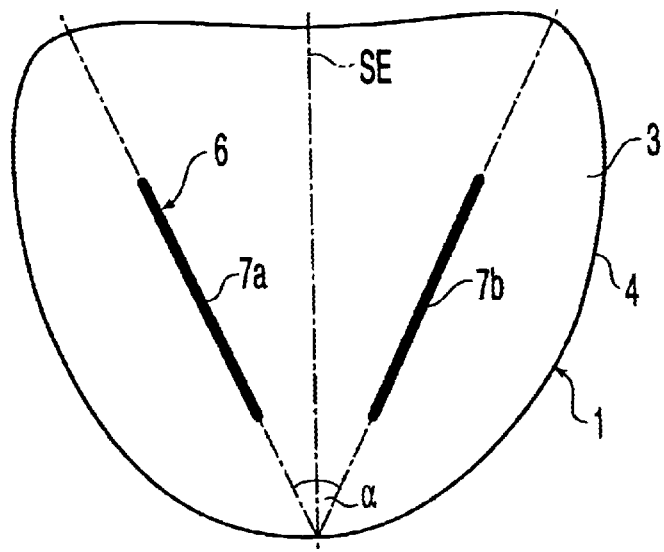
FIGS. 1 to 6 show a view of the back of first through sixth embodiment, respectively, of a symmetrical, heart-shaped breast prostheses having different notch shapes and notch arrangements in the unshaped state of the prosthesis.
Figure 7:
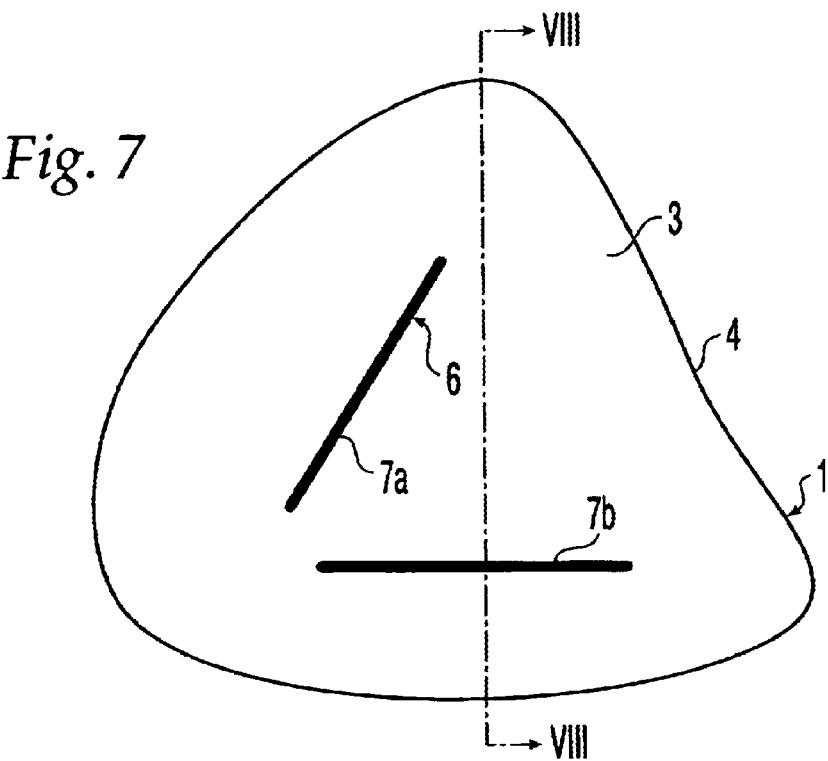
FIG. 7 shows a view of the back of the prosthesis having the notch shape and notch arrangement shown in FIG. 1, in the state when worn and when the wearer is in the upright position.
Figure 8:
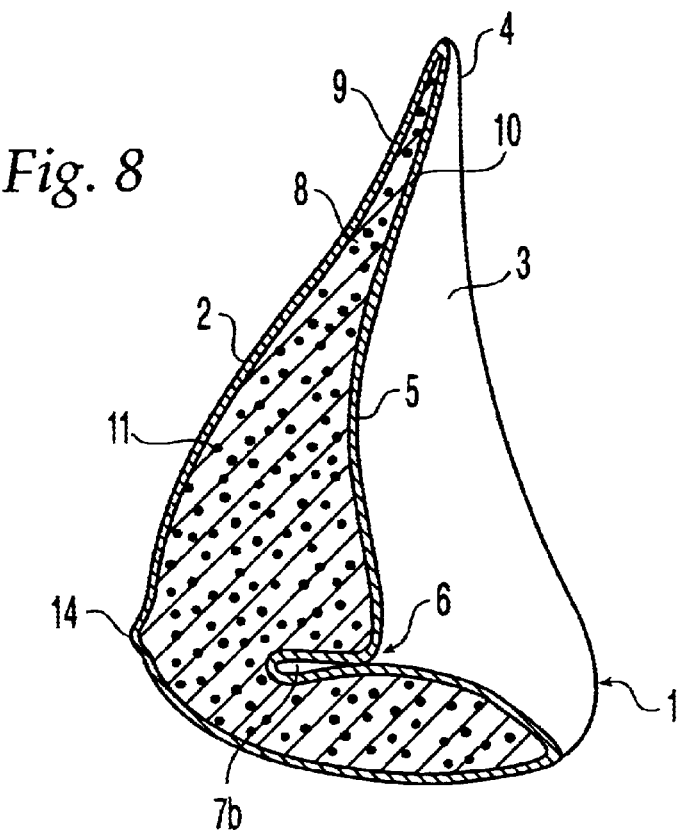
FIG. 8 shows a section along the sectional line VIII—VIII shown in FIG. 7.

As shown in FIGS. 1, 7 and 8, a symmetrical, heart-shaped breast prosthesis according to a first embodiment has a prosthesis body 1, which has a front 2, a back 3 and a prosthesis edge 4 which follows a closed line and at which the front 2 and the back 3 each end. The front 2 of the prosthesis body 1 has a shape corresponding to the shape of the natural breast. FIG. 1 shows the back of the prosthesis in the unshaped state of the prosthesis, in which it is present, for example, when it is in the cavity of the lower part of the mold in which it is produced. FIGS. 7 and 8, on the other hand, show the prosthesis in a shaped state which it assumes if it is worn in the right cup of a brassiere and the wearer is in the upright position. Compared with the state shown in FIG. 1, the breast prosthesis in the worn state, as shown in FIG. 7, is rotated by about 45° in the clockwise direction. If the breast prosthesis were worn in the left cup of a brassiere, the breast prosthesis would be rotated by about 45° in the counterclockwise direction starting from the view shown in FIG. 1.

The back 3 of the prosthesis is curved inwards and consequently forms a depression 5. As shown in FIGS. 1 to 6, one or more notches 6 in various shapes and arrangements is or are present at the back 3. The or each notch 6 is in each case symmetrical with respect to a plane of symmetry SE dividing the prosthesis body 1 into two equal halves.

In the embodiment shown in FIG. 1, a left notch 7a and a right notch 7b are provided, the two notches 7a and 7b being identical to one another and making an angle a of about 54° with one another. Depending on whether the breast prosthesis shown in FIG. 1 is worn on the left or right, the left notch 7a or the right notch 7b is transverse, i.e. essentially perpendicular, to the longitudinal axis of the wearer's body. In FIG. 7, the right notch 7b is essentially perpendicular to the sectional line VIII—VIII, which in turn is parallel to the longitudinal axis of the wearer's body because, in the view in FIG. 7, it is assumed that the breast prosthesis will be worn on the right side of the body.

The lines along which the notches 7a and 7b lie pass through the rounded corners of the prosthesis contour.

The notches 6 each reduce the cross-section of the prosthesis body 1, with the result that, in the region of the notches 6, the prosthesis body 1 forms a sort of hinge (film hinge) which expands or constricts depending on the position in which the breast prosthesis is worn, when the respective notch is transverse to the longitudinal axis of the wearer's body. In the view in FIG. 7, in which the notch 7b is transverse to the longitudinal axis of the wearer's body and the wearer assumes an upright position, the hinge of the prosthesis body 1, which is formed in the region of the notch 7b, constricts and does so, as shown in FIG. 8, in such a way that the opposite walls of the notch 7b rest one on top of the other.

When the wearer is in a prostrate position, the opposite walls of the notch 7b move apart or, in other words, the hinge formed in the region of the notch 7b expands and the prosthesis becomes flatter. In the state shown in FIGS. 7 and 8, the prosthesis has collapsed somewhat, the collapse being stopped by opposite walls of the notch 7b resting one against the other. In the collapsed state, the prosthesis branch which is the upper one in FIG. 7 has moved slightly downwards and that part of the prosthesis which corresponds to the lower region of the breast has become more convex.

The collapse and flattening of the prosthesis, which takes place according to the wearer's posture and which is permitted by the notches, occurs in a manner similar to that in the case of the prosthesis disclosed in U.S. Pat. No. 6,136,028. Furthermore, the shapes of the individual notches of the breast prosthesis according to the invention are formed similarly to those of the individual notches of the breast prosthesis disclosed in U.S. Pat. No. 6,136,028. The content of U.S. Pat. No. 6,136,028 is therefore incorporated by reference, to the extent necessary to understand the present invention.

A protuberance 14 simulating a nipple is formed in a known manner on the front 2 of the prosthesis.

Furthermore, the prosthesis body 1 is composed mainly of a flexible silicone rubber material 8 and a bag comprising two elastically extendable plastics films 9, 10 tightly welded to one another along the prosthesis edge 4, the silicone rubber material 8 being enclosed in the bag without cavities. The two plastics films 9, 10 are polyurethane films.

Figure 2:
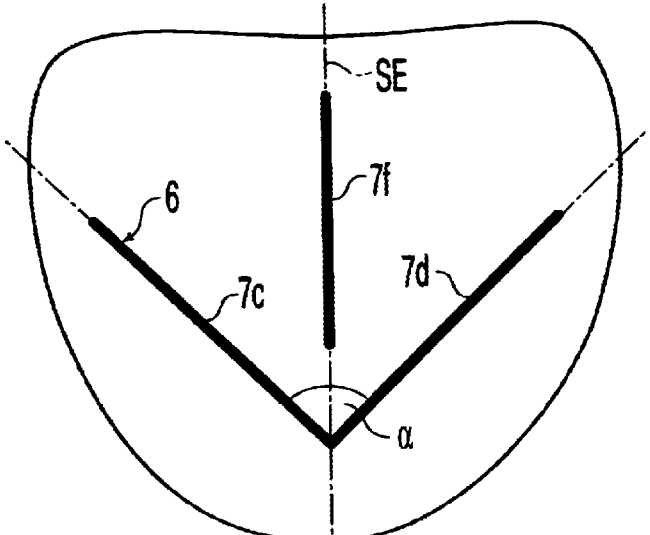

In the embodiment shown in FIG. 2, two notches 7c and 7d are provided, which terminate with their inner ends at the plane of symmetry SE and make an angle a of about 90° with one another. The notches 7c and 7d each lie along a line which intersects the heart-shaped prosthesis contour laterally below its rounded corners. A third notch 7f runs between the two notches 7c and 7d, along the plane of symmetry SE.

Figure 3:
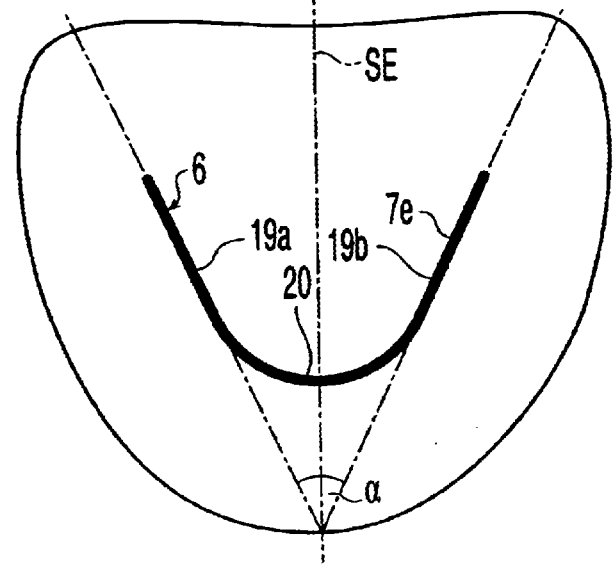

In the embodiment shown in FIG. 3, the first and second notches are connected by a rounded middle section 20 to thereby form a continuous V-shaped notch 7e. The V-shaped notch 7e is symmetrical with respect to the plane of symmetry and its limbs 19a 19b make an angle α of about 54° with one another.

Figure 4:
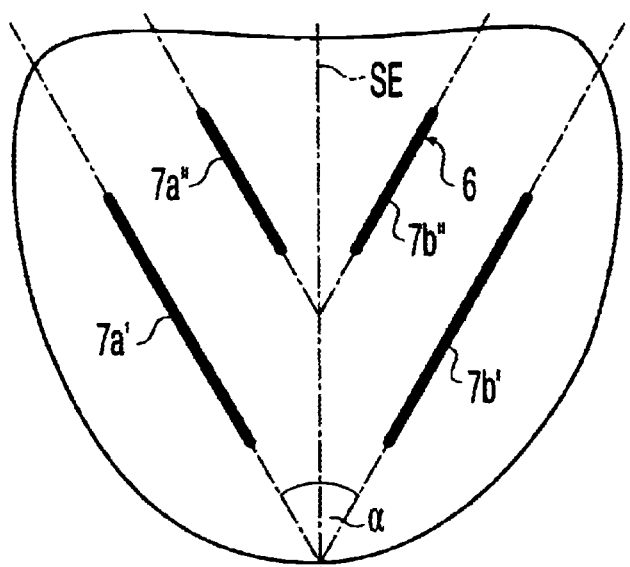

In the embodiment shown in FIG. 4, initially two notches 7a' and 7b' are provided, which are similar in shape and arrangement to the notches 7a and 7b of the embodiment of FIG. 1. In addition, two further notches 7a" and 7b", which in the view in FIG. 4 are arranged above the notches 7a' and 7b' and are each parallel to the notch 7a' and 7b', respectively, are provided in the embodiment of FIG. 4.

Figure 5:
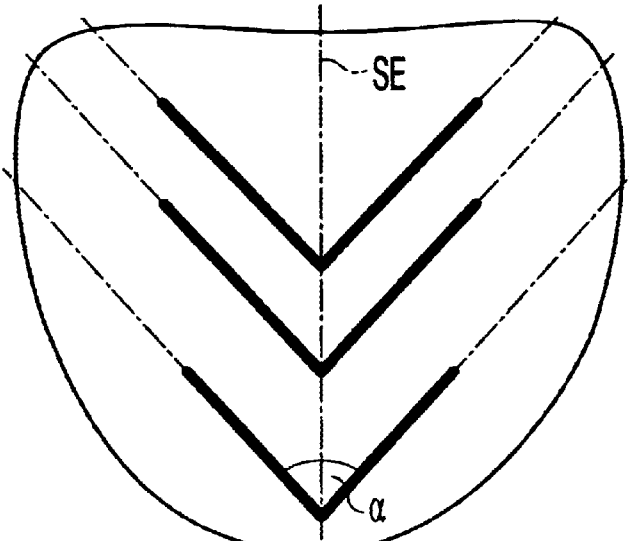

In the embodiment of FIG. 5, initially two notches 7c' and 7d' are provided, which are similar to the notches 7c and 7d of the embodiment of FIG. 2. In addition, two further pairs of notches 7c" and 7d", and 7c''' and 7d''', are provided in the embodiment of FIG. 5. The notches 7c', 7c" and 7c"are parallel to one another. The notches 7d', 7d" and 7d''' are likewise parallel to one another.

Figure 6:
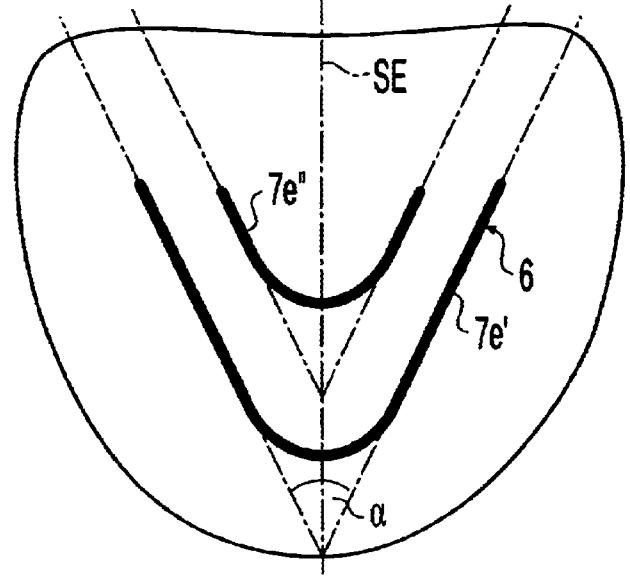

The embodiment shown in FIG. 6 initially has a notch 7e' which is similar to the notch 7e of the embodiment of FIG. 3. In addition, a notch 7e" is provided above the notch 7e in the embodiment of FIG. 6. The notch 7e" has the same V-shape as the notch 7e.

The notch shapes and notch arrangements are not limited to those of the embodiments shown in FIGS. 1 to 6. In the case of a plurality of notches, the various notch shapes and notch arrangements may also be combined with one another. Thus, for example, it is also possible for the notch shapes and notch arrangements shown in FIGS. 1, 2 and 3 to be combined with one another.

It is possible to add to the notches shown in FIGS. 1 to 6 also those which are parallel or perpendicular to the plane of symmetry SE. In all embodiments, however, it is important that at least one notch or at least one longer section of a notch is transverse to the longitudinal axis of the wearer's body when the prosthesis is worn.

A common feature of all embodiments is that the silicone rubber material is mixed with a filler comprising hollow spheres 11 which have a weight of 5 to 30% by weight, based on the weight of the silicone rubber material. Hollow spheres 11 may comprise of plastic or glass. The viscosity of the mixture consisting of the silicone rubber material and the filler is between 2500 and 8000 mPa·s.

The present invention has been described with reference to a particular embodiment in connection with a particular application. Those having ordinary skill in the art and access to the teachings of the present invention will recognize additional modifications and applications within the scope thereof. It is therefore intended by the appended claims to cover any and all such applications, modifications, and embodiments within the scope of the present invention.

What is claimed is:

1. A symmetrical breast prosthesis wearable in either the left or right cup of a brassiere or corselet following a mastectomy, comprising:
   a prosthesis body having a front shaped like a natural breast, and a concave back, a perimeter of the prosthesis body defining a substantially heart shaped contour; wherein:
      the heart-shaped contour has first and second rounded corners on either side of a plane of symmetry, the rounded corners being separated by a concave portion of said heart-shaped contour; and
      the concave back is provided with at least two continuous notches spaced apart from one another, each of said continuous notches comprising a rounded middle section that intersects said plane of symmetry, the rounded middle section being connected on either side to first and second limbs that extend in a direction away from said rounded middle section.

2. The symmetrical breast prosthesis according to claim 1, wherein the limbs define between them an angle (α) in the range between 30° and 90°.

3. The symmetrical breast prosthesis according to claim 2, wherein the limbs define between them an angle (α) in the range between 40° and 60°.

4. The symmetrical breast prosthesis according to claim 1, wherein the first and second limbs belonging to each continuous notch are curved.

5. The symmetrical breast prosthesis according to claim 1, wherein each of the continuous notches is symmetrical with respect to the plane of symmetry.

6. The symmetrical breast prosthesis according to claim 1, characterized in that the prosthesis body comprises a silicone rubber material that is mixed with a filler comprising hollow spheres which have a weight of from 5 to 30% by weight, based on the weight of the silicone rubber material.

7. The symmetrical breast prosthesis according to claim 6, wherein the silicone rubber material and the filler together form a mixture having a viscosity of between 2500 to 8000 mPas.

8. A symmetrical breast prosthesis wearable in either the left or right cup of a brassiere or corselet following a mastectomy, comprising:
   a prosthesis body having a front shaped like a natural breast, and a concave back, a perimeter of the prosthesis body defining a substantially heart shaped contour; wherein:
      the concave back is provided with at least a first pair of notches comprising first and second identical notches arranged symmetrically with respect to a plane of symmetry (SE) dividing the prosthesis body into two halves, the first and second notches defining between them an angle (α) in the range between 30° and 90°.

9. The symmetrical breast prosthesis according to claim 8, wherein the angle between the first and second notches is in the range of 40° to 60°.

10. The symmetrical breast prosthesis according to claim 8, wherein the angle between the first and second notches is about 90°.

11. The symmetrical breast prosthesis according to claim 8, wherein the prosthesis is configured such that the first notch is essentially perpendicular to a longitudinal axis of the wearer's body, when the prosthesis is worn in a left cup, and the second notch is essentially perpendicular to said longitudinal axis of the wearer's body, when the prosthesis is worn in a right cup.

12. The symmetrical breast prosthesis according to claim 8, wherein:
   the heart-shaped contour has first and second rounded corners on either side of a plane of symmetry, the rounded corners being separated by a concave portion of said heart-shaped contour.

13. The symmetrical breast prosthesis according to claim 12, wherein the first and second notches each extend in length along a line passing through one of said first and second rounded corners.

14. The symmetrical breast prosthesis according to claim 12, wherein the first and second notches each extend in length along a line which intersects the heart-shaped contour at a point which is laterally next to one of two rounded corners.

15. The symmetrical breast prosthesis according to claim 8, wherein the first and second notches meet at the plane of symmetry.

16. The symmetrical breast prosthesis according to claim 15, further comprising an additional notch (7f) extending along the plane of symmetry between the first and second notches.

17. The symmetrical breast prosthesis according to claim 8, further comprising an additional notch (7f) extending along the plane of symmetry between the first and second notches.

18. The symmetrical breast prosthesis according to claim 8, wherein the first and second notches are each curved.

19. The symmetrical breast prosthesis according to claim 8, further comprising:
   a second pair of notches provided on the back of the prosthesis body, the second pair being arranged symmetrically with respect to the plane of symmetry and being parallel to, and spaced apart from, corresponding notches belonging to the first pair of notches.

20. The symmetrical breast prosthesis according to claim 19, further comprising:
   a third pair of notches provided on the back of the prosthesis body, the third pair being arranged symmetrically with respect to the plane of symmetry and being parallel to, and spaced apart from, corresponding notches belonging to both the first and second pairs of notches.

21. The symmetrical breast prosthesis according to claim 19, wherein the first and second notches in each of the first, second, and third pairs of notches, meet at the plane of symmetry.

22. The symmetrical breast prosthesis according to claim 8, wherein the first and second notches are connected by a first rounded section to thereby form a first, continuous notch which is symmetrical with respect to the plane of symmetry.

23. The symmetrical breast prosthesis according to claim 22, further comprising a second pair of notches connected by a second rounded section to thereby form a second, continuous notch which is symmetrical with respect to the plane of symmetry and is spaced apart from the first, continuous notch.

24. The symmetrical breast prosthesis according to claim 8, characterized in that the prosthesis body comprises a silicone rubber material that is mixed with a filler comprising hollow spheres which have a weight of from 5 to 30% by weight, based on the weight of the silicone rubber material.

25. The symmetrical breast prosthesis according to claim 24, wherein the silicone rubber material and the filler together form a mixture having a viscosity of between 2500 to 8000 maPs.

26. The symmetrical breast prosthesis according to claim 24, wherein the hollow spheres comprise a plastic or glass.

* * * * *